United States Patent [19]

Ponchon et al.

[11] Patent Number: 5,635,214
[45] Date of Patent: Jun. 3, 1997

[54] SORBENT PRECIPITATED SILICA PARTICULATES

[75] Inventors: Jean-Luc Ponchon, Craponne; Lionel Rabute, Lyons, both of France

[73] Assignee: Rhone-Poulenc Chimie, Courbevoie Cedex, France

[21] Appl. No.: 662,982

[22] Filed: Jun. 13, 1996

Related U.S. Application Data

[63] Continuation of Ser. No. 393,254, Feb. 23, 1995, abandoned, which is a continuation of Ser. No. 353,048, May 17, 1989, abandoned.

[30] Foreign Application Priority Data

May 19, 1988 [FR] France .................. 88 06731

[51] Int. Cl.$^6$ .................. A61K 9/18; C01B 33/193
[52] U.S. Cl. .................. 424/489; 423/335; 423/338; 423/339; 424/421; 514/904; 514/951
[58] Field of Search .................. 423/335, 338, 423/339; 424/421, 489; 502/233, 407; 514/904, 951

[56] References Cited

U.S. PATENT DOCUMENTS

| | | | |
|---|---|---|---|
| 2,924,510 | 2/1960 | Allen | 423/335 |
| 3,210,273 | 10/1965 | Taulli | 252/28 |
| 3,445,189 | 5/1969 | Maat et al. | 423/325 |
| 3,914,430 | 10/1975 | Cannalonga et al. | 514/458 |
| 3,947,596 | 3/1976 | Cannalonga et al. | 514/725 |
| 3,959,472 | 5/1976 | Cannalonga et al. | 514/251 |
| 3,962,384 | 6/1976 | Cannalonga et al. | 264/7 |
| 3,967,563 | 7/1976 | Wason | 106/492 |
| 4,001,379 | 1/1977 | Turk et al. | 423/339 |
| 4,224,295 | 9/1980 | Brandt et al. | 423/335 |
| 4,230,765 | 10/1980 | Takahashi et al. | 428/283 |
| 4,590,052 | 5/1986 | Chevallier et al. | 423/335 |
| 4,603,143 | 7/1986 | Schmidt | 514/458 |
| 4,617,294 | 10/1986 | Krivak et al. | 514/52 |
| 4,704,425 | 11/1987 | Lagarde et al. | 524/492 |
| 4,717,561 | 1/1988 | Krivak et al. | 423/335 |
| 4,775,540 | 10/1988 | Hertel et al. | 426/74 |
| 4,820,532 | 4/1989 | Bayer et al. | 426/74 |
| 4,842,838 | 6/1989 | Chevallier | 423/339 |
| 4,857,289 | 8/1989 | Nauroth et al. | 423/339 |
| 4,870,196 | 9/1989 | Thorengaard | 549/410 |
| 5,011,690 | 4/1991 | Garvey et al. | 424/401 |
| 5,236,683 | 8/1993 | Nakazawa et al. | 423/335 |

OTHER PUBLICATIONS

Kirk–Othmer Encyclopedia of Chemical Technology. 3rd Edition, Published by John Wiley & Sons, N.Y., (1982), vol. 20, pp. 748–781.

Ullmann's Encyclopedia of Industrial Chemistry, 5th Edition, Published by VCH Verlagsgesellschaft mbH, Weinheim, DE, (1993), pp. 583, 584, 642–647.

*Primary Examiner*—John C. Bleutoe
*Assistant Examiner*—Robert H. Harrison
*Attorney, Agent, or Firm*—Burns, Doane, Swecker & Mathis, L.L.P.

[57] ABSTRACT

Novel precipitated silica particulates, well suited for conditioning/sorbing a wide variety of liquid active agents thereon, e.g., the vitamins, have (i) a BET surface area of at least 170 m$^2$/g; (ii) an oil absorption (DOP) ranging from 220 to 300 ml/g; (iii) a fill density in the packed state of at least 0.29; (iv) a mean particle diameter ranging from 80 to 150 μm; and (v) a maximum grain size distribution index of 0.70.

21 Claims, No Drawings

SORBENT PRECIPITATED SILICA PARTICULATES

This application is a continuation of application Ser. No. 08/393,254, filed Feb. 23, 1995, which is a continuation of application Ser. No. 07/353,048, filed May 17, 1989, both now abandoned.

BACKGROUND OF THE INVENTION

1. Field of the Invention

The present invention relates to novel absorbent precipitated silica particulates and to various compositions of matter based on such absorbent silica particulates.

2. Description of the Prior Art

It is known to this art to condition various liquids by depositing them onto a particulate silica support. The purpose of such conditioning is to convert a liquid that cannot easily be manipulated, or is manipulated only with difficulty, into a fluid powder that is readily stored, for example in bags, and which is both readily dispersed and also mixed with other divided solid materials.

The compositions formulated in this manner, i.e., a liquid absorbed onto a silica support, will hereinafter be referred to as "conditioned" compositions.

These compositions must have a high content in active agent, together with a high density. They must be easily handled, which implies easy pouring and low dusting. These different requirements are sometimes contradictory and competing. It is apparent that such properties closely depend on the nature of the silica employed as the support substrate.

SUMMARY OF THE INVENTION

Accordingly, a major object of the present invention is the provision of improvedly absorbent silica particulates and conditioned compositions comprised thereof.

Another object of this invention is the provision of conditioned compositions comprised of such improved silica particulates which have a high density, improved pouring properties and which are less susceptible to dusting.

Briefly, the novel precipitated silica particulates of the present invention have the following characteristics:

(i) a BET surface area of at least 170 m$^2$/g;

(ii) an oil absorption (DOP) ranging from 220 to 300 ml/g;

(iii) a fill density in the packed state of at least 0.29;

(iv) a mean particle diameter ranging from 80 to 150 μm; and (v) a maximum grain size distribution index of 0.70.

DETAILED DESCRIPTION OF THE PREFERRED EMBODIMENTS OF THE INVENTION

More particularly according to the present invention, it has now unexpectedly and surprisingly been determined that the combination of the above properties and characteristics provides an absorbent silica material that is especially well suited as a support substrate for conditioning a wide variety of liquids.

It will of course be appreciated that this invention also features such conditioned compositions, per se, comprising liquid materials adsorbed onto support substrates containing the subject novel precipitated silica particulates.

The silica particulates of this invention have especially desirable properties due to the combination of characteristics more fully described below.

First, the silica has a BET surface area of at least 170 m$^2$/g, and preferably at least 210 m$^2$/g. In particular, such BET surface area advantageously ranges from 170 to 400 m$^2$/g and preferably from 210 to 400 m$^2$/g.

The BET surface area is determined by the method of Brunauer-Emmet-Teller described in the *Journal of the American Chemical Society*, Vol. 60, page 309 (February 1938) and the standard, NF T45007 (5.11).

Another characteristic of the silica according to the invention is its oil absorption. Such oil absorption (DOP), determined by the standard NFT 30-022 (March 53) using dioctyl phthalate, ranges from 220 to 300 ml/100 g, preferably from 220 to 280 and more preferably from 240 to 280 mg/100 g.

Its density is at least 0.29. This is the fill density in packed state (DRT) according to the standard AFNOR No. 030100. More preferably, such density ranges from 0.29 to 0.4 and more preferably from 0.29 to 0.36.

Lastly, grain or particle size distribution is also an important characteristic of the silica particulates according to the invention.

This grain size distribution is such that the mean diameter $d_{50}$ of the particles ranges from 80 to 150 μm and more preferably from 90 to 130 μm.

The grain size distribution is determined by screen retention in the dry state, according to the standard NF X11.507.

Furthermore, the grain size distribution of the silica particulates according to the invention is restricted. This may be expressed by an index of dispersion (I.D.) of a maximum of 0.70, more preferably of a maximum of 0.6. This index corresponds to a ratio of $(d84-d16)/2d50$, in which $dn$ is the diameter for which there are $n$ % of particles of a size less than the value of said mean diameter.

In certain preferred embodiments of the invention, the silica may have supplementary and additional properties.

The silica particulates according to the invention generally have a pH ranging from 4 to 8 and more preferably ranging from 5.5 to 7. This pH is determined according to the standard NFT-45007 (5.5).

Further, the silica particulates according to the invention preferably have a maximum ignition weight loss of 13% of the material, per se, and a maximum ignition weight loss of 6% of the dry solids [NFT standard 45007 (5.3)].

The silica particulates may be prepared by any known technique, such as by reacting a silicate with an acidifying agent, for example an inorganic acid of the carbonic, sulfuric or hydrochloric type. Thus, various processes may be employed entailing the addition of an acid to a silicate base, or the simultaneous total or partial addition of the acid and the silicate to a water base, whether or not in the presence of a salt or solution of silicate.

It may be advantageous to carry out appropriate post-treatment, i.e., introducing into the reaction medium, after an initial precipitation, a solution of silicate and/or of an acid.

Following the filtration of the reaction slurry, a filter cake is recovered, which is optionally washed. The filter cake is then typically comminuted and ultimately dried.

During the comminution and optionally during any subsequent stage in the process for the preparation of the subject silica particulates, it is advantageous to add an aluminum compounds to the cake or the reaction medium, which addition renders the suspension less viscous and more easily pumpable. In this respect, compare FR 2,536,380, hereby incorporated by reference.

Preferably, the process conditions should be such that the cake, in particular in the comminuted state, should have a maximum ignition weight loss of 77%, preferably at most 75%, prior to drying.

It will be appreciated that this ignition weight loss value may be adjusted by the addition to the cake, in particular during the comminution, of previously dried silica particulates.

The drying of the cake to provide the desired final product may be carried out by any known means, such as, for example, by atomization and, more particularly, utilizing a turbine atomizer.

The sorbent silica particulates of the invention are especially suitable for the conditioning of liquids and, thus, for the preparation of conditioned compositions.

A very large number of liquids may be deposited onto the subject silica support in this manner. Exemplary thereof are the organic acids, surface active agents of the anionic type used in detergents, such as sulfonates, or of the nonionic type, such as alcohols or phenols, as well as vulcanization accelerators and antioxidants for use in the rubber industry.

More particularly representative are those liquids employed as supplements in human or animal foodstuffs.

Specifically, the vitamins, and particularly the vitamins A, B, C, D, E and K may thus be conditioned.

Among the B vitamins, more particularly representative are choline and its derivatives, specifically choline hydrochloride.

The absorption of the liquid onto the support is carried out in any known manner, for example by pulverizing the liquid onto the silica particulates in a mixer.

The amount of liquid absorbed is a function of the desired end-application. The silica particulates of the invention make it possible to produce compositions having a liquid content in excess of 50% by weight and even up to 70% by weight, for example ranging from 50% to 60% by weight.

In general, the silica particulates according to the invention provide conditioned compositions having a high density, very good flowability and reduced dusting.

For example, in the particular cases of vitamin E and choline hydrochloride, the DRT (packed density) of the compositions may be at least 0.60, more particularly at least 0.65 and even at least 0.70.

The angle of repose of the subject compositions (according to the standard NFT 20221) is a maximum of 32°.

The dusting index of such compositions is less than 2, or even less than 1.

Dusting is measured by the apparatus described in FR 87/03,159, hereby also incorporated by reference.

The apparatus is connected with a micro-current system converting the variation in the resistance of the photoelectric cell into a potential, displayed graphically in the form of a peak on a graphic plotter graduated from 1 to 100 mV. The value, in mV, of the peak constitutes the dusting index (IP).

For purposes of comparison, compositions of the same type, but formulated from the silica supports of the prior art, have an IP of at least 3.

Compositions conditioned with vitamins preferably have a maximum dispersion index, as defined above, of 0.55.

In order to further illustrate the present invention and the advantages thereof, the following specific examples are given, it being understood that same are intended only as illustrative and in nowise limitative.

EXAMPLE 1

This example describes the preparation of the absorbent silica particulates according to the invention.

Sulfuric acid was added to a sodium silicate base in a ratio of 3.5, at a temperature of 70° C. The pH of the silica slurry formed was adjusted to a value of 5. The slurry was then filtered and the wet filter cake washed and then comminuted.

During comminution, a fraction of previously dried silica was added to provide a comminuted cake having an ignition weight loss of 75%. The pH was then adjusted to 6.0.

The comminuted cake was dried by atomization. Silica particulates having the following properties were obtained:

pH=6.7
DRT=0.32
$d_{50}$=105 μm
DOP=250 ml/100 g
BET=270 m$^2$/g
ID=0.5

EXAMPLE 2

In this example, the silica particulates of Example 1 were used as a support for vitamin E.

The vitamin E was deposited onto the support in a 7 liter V-mixer rotating at 20 rpm, having an inner axle rotating at 1,900 rpm, equipped with plates over which the vitamin E was sprayed and on which breaker blades were mounted.

The entirety of the silica described above was charged into the mixer and then the vitamin was sprayed onto the silica. Mixing was continued for 15 min and the mixture was homogenized for an additional two minutes.

The vitamin was incorporated at a temperature of 70° C. and at a constant rate of 100 ml/min.

In the final mixture, the proportions by weight were 46% SiO$_2$ and 54% d,1-alpha-tocopherol acetate.

A composition having the following characteristics was obtained:

DRT=0.70
$d_{50}$=90 μm
ID=0.55
Angle of repose=30°
IP=1

EXAMPLE 3

This example describes the preparation of a second absorbent silica according to the invention.

The procedure of Example 1 was repeated. However, after completion of the reaction, a supplemental treatment was carried out by introducing a solution of sodium silicate and sulfuric acid into the reaction medium.

The filter cake was washed and comminuted, and a fraction of previously dried silica was added such as to provide an ignition weight loss of the comminuted cake of 74% Sodium aluminate (4,000 ppm by weight relative to the anhydrous silica) was also added, which rendered the suspension more pumpable. The pH was adjusted to 6 and the suspension dried as in Example 1.

Silica particulates having the following characteristics were obtained:

pH=7.0
DRT=0.34
ID=0.5
DOP=240 ml/100 g
$d_{50}$=100 μm
BET=220 m$^2$ g

EXAMPLE 4

Deposition onto the silica was carried out as in Example 2, but choline hydrochloride was deposited onto the silica particulates of Example 3.

The proportions in the final compositions were as follows: 60 parts by weight of a 70% aqueous solution of choline hydrochloride, 40 parts of silica particulates, 0.3 parts of an additive (magnesium stearate).

The compositions had the following characteristics:

DRT=0.77

Angle of repose=31°

$d_{50}$=90 μm

IP=1.6

ID=0.5

COMPARATIVE EXAMPLE 5

As the support material, a silica marketed by the RHONE-POULENC Co. under the trademark Tix-O-Sil 38A, and having the following characteristics, was used:

pH=7

DRT=0.22

$d_{50}$=60 μm

ID>0.7

DOP=340 ml/100 g

BET=330 m$^2$/g

A conditioned composition based on vitamin E was prepared under the conditions of Example 2; it had the following characteristics:

DRT=0.50

$d_{50}$=80 μm

ID>0.7

Angle of repose=41°

IP>5

It will be seen that, relative to Example 1, this composition had lesser flowability and was much more dusting.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Sorbent precipitated silica particulates having the following properties:

(i) a BET surface area of at least 170 m$^2$/g;

(ii) an oil absorption (DOP) ranging from 220 to 280 ml/100 g;

(iii) a fill density in the packed state of at least 0.29;

(iv) a mean particle diameter ranging from 80 to 150 μm; and (v) a maximum grain size distribution index of 0.70.

2. The silica particulates as defined by claim 1, having a BET surface area of at least 210 m$^2$/g.

3. The silica particulates as defined by claim 2, having a BET specific surface area ranging from 210 to 400 m$^2$/g.

4. The silica particulates as defined by claim 1, having a pH ranging from 4 to 8.

5. The silica particulates as defined by claim 1, having a fill density in packed state ranging from 0.29 to 0.4.

6. The silica particulates as defined by claim 5, having a fill density in packed state ranging from 0.29 to 0.36.

7. The silica particulates as defined by claim 1, having a mean particle diameter ranging from 90 to 130 μm.

8. The silica particulates as defined by claim 1, having a maximum index of dispersion of 0.70.

9. The silica particulates as defined by claim 8, having a maximum index of dispersion of 0.6.

10. The silica particulates as defined by claim 4, having a pH ranging from 5.5 to 7.

11. The silica particulates as defined by claim 1, having a maximum ignition weight loss of 13%.

12. A high density, flowable and conditioned composition of matter, comprising a support substrate of the silica particulates as defined by claim 1, said silica particulates having sorbed thereon a liquid active agent.

13. The composition of matter as defined by claim 12, said liquid active agent comprising a liquid dietary supplement.

14. The composition of matter as defined by claim 13, said liquid dietary supplement comprising a vitamin.

15. The composition of matter as defined by claim 14, said liquid dietary supplement comprising vitamin A, B, C, D, E or K.

16. The composition of matter as defined by claim 13, said liquid dietary supplement comprising choline hydrochloride.

17. The composition of matter as defined by claim 12, wherein said liquid active agent is an organic acid, a surfactant, a vulcanization accelerator or an antioxidant.

18. The composition of matter as defined by claim 12, having a maximum angle of repose of 32°.

19. The composition of matter as defined by claim 12, comprising at least 50% by weight of said liquid active agent.

20. The composition of matter as defined by claim 12, having a dusting index of less than 2.

21. The composition of matter as defined by claim 20, having a dusting index of less than 1.

* * * * *